United States Patent
Koudil et al.

(10) Patent No.: US 8,519,171 B2
(45) Date of Patent: *Aug. 27, 2013

(54) SEPARATION IMPROVEMENT IN A METHOD OF PRODUCING ALKYL ESTERS FROM VEGETABLE OR ANIMAL OIL AND AN ALIPHATIC MONOALCOHOL

(75) Inventors: Abdelhakim Koudil, Lyons (FR); Romain Rousset, Oullins (FR); Laurent Bournay, Chaussan (FR); Vincent Coupard, Valencin (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 524 days.

This patent is subject to a terminal disclaimer.

(21) Appl. No.: 12/667,146

(22) PCT Filed: Jun. 9, 2008

(86) PCT No.: PCT/FR2008/000781
§ 371 (c)(1),
(2), (4) Date: Jul. 28, 2010

(87) PCT Pub. No.: WO2009/007528
PCT Pub. Date: Jan. 15, 2009

(65) Prior Publication Data
US 2010/0286436 A1    Nov. 11, 2010

(30) Foreign Application Priority Data
Jun. 29, 2007 (FR) ..................... 07 04715

(51) Int. Cl.
*C11C 3/00* (2006.01)
*B01J 19/00* (2006.01)

(52) U.S. Cl.
USPC ............ 554/169; 422/198; 554/124; 554/175

(58) Field of Classification Search
USPC .......................... 554/124, 169, 175; 422/198
See application file for complete search history.

(56) References Cited

U.S. PATENT DOCUMENTS 5,424,467 A * 6/1995 Bam et al. ............... 554/216
5,908,946 A 6/1999 Stern et al.
6,878,837 B2 4/2005 Bournay et al.

FOREIGN PATENT DOCUMENTS

EP 1 352 893 A 10/2003
FR 2 752 242 A 2/1998
GB 2 174 697 A 11/1986

* cited by examiner

*Primary Examiner* — Yate K Cutliff
(74) *Attorney, Agent, or Firm* — Millen, White, Zelano & Branigan, P.C.

(57) ABSTRACT

The present invention describes a method of producing fatty acid alkyl esters and glycerin implementing, in a reaction section, a set of transesterification reactions between a vegetable or animal oil and an aliphatic monoalcohol, and using a heterogeneous solid catalyst, comprising:
  a) a glycerin phase introduction stage,
  b) an excess alcohol evaporation stage, and
  c) a glycerin phase decantation stage.

The supernatant ester phase obtained after decantation is then optionally sent to a coalescer, also allowing separation of the glycerin, then to a purification stage by adsorption on solids. This improved method prevents microemulsion formation.

12 Claims, 2 Drawing Sheets

SEPARATION IMPROVEMENT IN A METHOD OF PRODUCING ALKYL ESTERS FROM VEGETABLE OR ANIMAL OIL AND AN ALIPHATIC MONOALCOHOL

FIELD OF THE INVENTION

The invention relates to an improved method of producing alkyl esters from vegetable or animal oils and an aliphatic monoalcohol.

BACKGROUND OF THE INVENTION

Vegetable oil alkyl esters intended to be used as biofuel are produced from vegetable oils obtained for example from rapeseed, sunflower, soybean or even palm. Ill-suited for directly feeding modern diesel engines of private cars, vegetable oils essentially consisting of triglycerides have to be converted by means of a transesterification reaction with an alcohol, methanol or ethanol for example, introduced in excess to produce vegetable oil methyl esters (VOME) and glycerin.

What is referred to as glycerol is the pure body of chemical formula $C_3H_8O_3$ and glycerin or glycerin phase is understood to be a mixture predominantly containing glycerol and other impurities, such as water, methanol, mono-, di- and triglycerides for example, mono- and diglycerides being triglycerides partly converted by the transesterification reaction.

The Esterfip-H™ process developed by IFP allows to obtain a biodiesel and a glycerin of very good quality, with high yields. The flowsheet of this process consists of two fixed-bed transesterification reactors using a solid heterogeneous catalyst, operating on a continuous basis and arranged in series, which allows conversion to be maximized. The effluent from the first reactor is subjected to partial evaporation so as to remove the excess methanol introduced and thus to promote separation of the glycerin formed while favourably shifting the reaction equilibrium in order to maximize conversion in the second reactor. After the second transesterification reaction, the major part of the excess methanol is removed by evaporation (more than 99%) and recycled. The insoluble glycerin is eliminated by decantation and a final methyl ester purification stage consists in removing the soluble glycerin by passage through a column filled with a selective adsorbent. The water content of the reaction medium is controlled so as to remain below a given limit value as described in U.S. Pat. No. 6,878,837 filed by the applicant.

The current European standard EN 14,214 for biofuels sets maximum methanol, water, free glycerol, mono-, di- and triglyceride contents: 0.2% by mass for methanol, 500 mg/kg for water, 0.02% by mass free glycerol, 0.8% by mass monoglycerides, 0.2% by mass di- and triglycerides.

Free glycerol, as opposed to bonded glycerol, is defined as a glycerol molecule totally detached from any carbon chain and of formula $C_3H_8O_3$.

Glycerol is referred to as bonded when the functional group of glycerol $C_3H_8O_3$ is alkylated to one or more fatty acid chains giving monoglyceride, diglyceride or triglyceride molecules.

In the Esterfip-H™ process diagrammatically shown in FIG. 1 as described in the prior art, stream A at the reaction section outlet predominantly contains methyl esters, methanol, glycerol and partly converted glycerides (monoglycerides, diglycerides and triglycerides), as well as water as traces, an impurity present in the feed. The conversion reached in this reaction section (two reaction stages with an intermediate stage of separation of the glycerin coproduced) allows to obtain partial glyceride contents compatible with the European standard for biodiesel.

In the particular case of the Esterfip-H™ process, the methyl esters and the glycerol are very poorly soluble and the methanol present acts as a co-solvent. Therefore, the higher the temperature and the methanol content, the higher the glycerol content of the ester phase.

Besides, pure glycerol has a density close to $1.2\ g \cdot cm^{-3}$, whereas for the ester it is around $0.9\ g \cdot cm^{-3}$. In the presence of a small proportion of methanol, the phase predominantly containing glycerol is therefore denser than the ester phase and it thus tends to come below the latter under the effect of gravity. The ester phase thus is the supernatent phase.

Separation of the methanol from stream A coming from the reaction section (not shown in the figure) is achieved by evaporation in two stages, the second one under vacuum, in order to reach methanol and water contents allowed by the standard (zone (1) in FIG. 1), stream B corresponding to the evaporated methanol. The methanol acting as a co-solubilizing agent for the methyl esters and the glycerol, this evaporation stage makes part of the glycerol present in this stream, in a proportion ranging between 0.1 and 5% by mass, insoluble. The soluble part represents, at ambient temperature, 500 to 700 ppm mass, the allowable maximum content set by the European standard being 200 ppm mass of free glycerol. Both the insoluble glycerol and part of the soluble glycerol therefore have to be separated. This separation is then carried out in several stages.

An important problem encountered during this excess alcohol evaporation stage and consequently upon formation of a two-phase medium (ester phase with dissolved glycerol droplets and glycerin phase) is the formation of microemulsions.

A microemulsion can generally be obtained through exterior energy supply, for example by applying a very high shear to a mixture of two liquids, or by applying an ultrasonic wave to the mixture.

A microemulsion can also appear spontaneously (P. Brochette, Emulsification "Elaboration et etude des emulsions", Techniques de l'Ingénieur, traité de Génie des procédés, J 2150), without any additional exterior energy supply, when some concentration conditions are met for each phase of the mixture. One then speaks of a spontaneous nucleation of the discontinuous phase initially dissolved in the continuous phase.

In the case of the ester phase/glycerol/alcohol ternary system obtained at the reaction section outlet of the Esterfip-H™ process, the alcohol, which is methanol, acts as a co-solubilizing agent. The progressive disappearance of the alcohol induced by a controlled evaporation leads to local oversaturation of the ester phase with glycerol. The saturation excess glycerol settles around what is referred to as nuclei consisting of surfactants: this phenomenon is called nucleation. The monoglycerides present in the effluent act as surfactants (<<Synthesis of Surfactants from Vegetable Oil Feedstocks>>, R. A. Holser, chp 10, Industrial Uses of Vegetable Oils, AOCS Press, 2005). The presence of surfactant compounds, even in very small proportions (of the order of 1 ppm), and the low interface tensions lead to the formation of very small micrometric droplets. This droplet creation occurs without requiring any other energy than the energy that tends to restore a ternary equilibrium broken as a result of the progressive disappearance, not necessarily complete, of one of the three compounds of the ternary mixture, methanol here.

The formation of microemulsions leads to the presence of a large population of glycerol microdroplets dispersed and dissolved in the ester phase.

In the Esterfip-H™ process as described in the prior art, separation of the glycerin phase occurs through gravity decantation in a decanter drum. This stage consists in sending this stream to a decanter drum 3 whose purpose is to allow the glycerin phase droplets, denser than the ester phase, to fall under the effect of gravity.

In general terms, the size of the decanter drum and the residence time of the feed in this device define the cleavage threshold of the decanter. The cleavage threshold is expressed in µm and it corresponds to the minimum drop size that can be separated by decantation in the drum. Below this threshold, the droplets do not settle rapidly enough in the decanter and they are carried along with the ester phase to the next stages of the process. Now, too long decantation times require longer effluent immobilization, thus leading to expensive overstocking and losses as regards the process profitability.

If the cleavage threshold is around 100 µm, the decantation times are fast, of the order of less than one hour (<<Extraction liquide-liquide>>, Description des appareils, J. Leybros, Techniques de l'ingénieur, Traité génie des procédés, J2764). If the cleavage threshold is below 10 µm, the decantation times become very long and the cost of the facility is significantly increased.

The decanter drum can come in form of a capacity of cylindrical shape whose axis of symmetry is horizontal. Stream D containing the ester with glycerin phase drops is injected at one end of the drum. Two outlets are arranged at the end of the drum: one is located on the upper generatrix to collect the supernatent ester phase, the other is Located at the bottom of the decanter drum to collect the glycerin phase. The ester stream containing the glycerin droplets is thus going to flow through the decanter drum horizontally from the inlet to the outlets at a velocity depending on the section and therefore on the diameter of this drum. During this horizontal flow, the glycerin drops tend to fall, under the effect of gravity, to the bottom of the decanter drum where they coalesce, i.e. they gather to form a continuous glycerin phase that can be withdrawn (stream F). The ester phase depleted in glycerin drops is withdrawn at the top of the drum (stream E).

When the microemulsion formation phenomenon that takes place during the alcohol evaporation stage is significant, separation by gravity decantation is not sufficient and the droplets of smaller size are still carried along to the next stages of the process.

In the Esterfip-H™ process, ester stream E leaving the decanter is sent to a coalescer (4). This equipment allows the glycerin droplets whose size was not large enough for decanting in the previous stage and that were consequently carried along to the decanter outlet to meet so as to form larger droplets that can then settle efficiently. Glycerin phase stream G is withdrawn at the bottom point of the coalescer. In theory, at the outlet of this equipment, ester stream H contains no more insoluble glycerin. However, too large a proportion of glycerin carried along to the decanter outlet upstream increases the coalescence difficulty and requires using a bigger equipment, which will therefore require a larger amount of steel and bigger tools. It will therefore be more expensive.

Coalescers are systems allowing the size of fine droplets to be increased by promoting the coalescence phenomenon, i.e. the formation of larger droplets (Perry's Chemical Engineers' Handbook, 7$^{th}$ Edition, Chp 15-17 "Liquid-liquid extraction equipment"). Once bigger, the droplets can be separated more readily by decantation for example. Coalescers are fibrous or porous solid beds whose properties are selected depending on the system to be separated. In general, cotton and glass fibers are used.

Like any industrial material, coalescers do not achieve perfect separation or they may operate under degraded working conditions (very high flow rate, aging, fouling, etc.). A proportion of fine droplets can pass through the coalescent medium. The larger the number of small-size droplets at the equipment inlet, the larger this proportion.

In order to reach the content allowed by the fuel specification, the glycerin dissolved in the ester phase still has to be separated. This stage is carried out in zone (5) by adsorption on solids, for example ion-exchange resins. These solids operate by alternating adsorption and regeneration cycles. At the end of this stage, the glycerin content of ester phase I thus meets the fuel specification (below 200 ppm).

The final ester processing chain thus comprises a decanter (3) for separating the major part of the glycerin, a coalescer (4) intended for the insoluble residual glycerin and a solid adsorption zone (5) for separating the glycerin dissolved in ester phase I. The main separation stage takes place in the decanter, whereas the stages that are conducted in the coalescer or in the solid adsorption zone are finishing stages.

In the Esterfip-H™ process as described in the prior art, the solids arranged in adsorption zone (5), ion-exchange resins for example, are in contact with part of the insoluble glycerin. Now, their use is all the more optimized as the proportion of insoluble glycerol to be separated from the ester phase is small. In the presence of too large an amount of glycerol, the solids used in the adsorption zone therefore tend to saturate more rapidly. The frequency of the adsorption/regeneration cycles increases. Regeneration is achieved using a solvent, preferably methanol. Now, repeated alternation of these cycles considerably reduces the life of these solids. For optimized operation of the solids, at the coalescer outlet, stream H should not contain more than 500 to 700 ppm mass of soluble glycerol.

The present invention thus provides a simple and improved flowsheet allowing the aforementioned drawbacks to be overcome, wherein the glycerin separation efficiency is improved while avoiding microemulsion formation during the evaporation stage. Thus, the efficiency of the decantation stage is improved. Now, this stage precisely conditions the dimensioning of the facilities required for the next stages of the process. Thus, increasing the decanter efficiency allows to reduce the size of the coalescer and to increase the efficiency thereof. The amount or the cycle time of the solids used in the adsorption zone, ion-exchange resins for example, is thus increased.

SUMMARY OF THE INVENTION

The present invention describes a method of producing vegetable or animal oil alkyl esters and glycerin wherein separation between the ester phase and the glycerin is markedly improved. The population of small-size glycerin droplets is considerably reduced by means of a stage of addition of a glycerin phase prior to the excess alcohol evaporation stage. Addition of a glycerin phase thus prevents the appearance of microemulsions and consequently facilitates the decantation stage.

The invention describes the facility wherein the method of producing vegetable or animal oil alkyl esters and glycerin with improved separation between the ester phase and the glycerin is carried out.

DETAILED DESCRIPTION

The present invention describes a method of producing fatty acid alkyl esters and glycerin implementing, in a reaction section, a set of transesterification reactions between a vegetable or animal oil and an aliphatic monoalcohol, and using a heterogeneous solid catalyst, comprising:

a) a stage of adding a glycerin phase of purity above 50% by mass in the effluent from the reaction section comprising alkyl esters, glycerol, partly converted triglycerides and alcohol, b) an excess alcohol evaporation stage, c) a cooling stage, and d) a stage of decanting the glycerin phase and obtaining a supernatant ester phase.

The glycerin phase addition stage is preceded by a stage of pre-evaporation of part of the excess alcohol.

At the end of the decantation stage, the ester phase obtained can be sent to one or more residual glycerin separation stages. Advantageously, this subsequent separation first takes place in a coalescer from which a glycerin phase and an ester phase greatly depleted in insoluble glycerin are extracted. The ester phase is then sent to at least one solid adsorption zone to separate the soluble glycerin and thus to obtain an ester phase meeting the fuel specifications.

The method according to the present invention thus allows to improve notably glycerin separation. This is due to the fact that the method according to the present invention allows to prevent the appearance of microemulsions during the excess alcohol evaporation stage and consequently to considerably decrease the population of microdroplets whose separation by gravity decantation would require equipments of very large size.

According to the method of the invention, the decantation front separating the glycerin from the ester phase thus progresses more rapidly in the presence of added glycerin. In other words, the invention allows to optimize the decantation stage (decanter size, residence time, production) and also the possible subsequent residual glycerin separation stages according to the operator's needs.

Introducing a "free" glycerin phase into the effluent from the reaction section allows to limit local oversaturations of the ester phase with glycerol, which cause microemulsion formation.

This glycerin phase supply can be achieved in two ways:

either a "free" glycerin phase is injected prior to alcohol evaporation so as to be in the zone of coexistence of two phases in the ester/glycerol/alcohol ternary diagram. The glycerol in oversaturation in the ester phase because of the progressive disappearance of the alcohol necessarily goes into the pre-existing glycerin phase, which prevents the formation of any microemulsion, or "free" glycerin is injected as close as possible to the evaporators so as to be in a single-phase zone of the ester/glycerol/alcohol ternary diagram. Once in the evaporator, the glycerin released as a result of alcohol evaporation allows to be in the zone of coexistence of the two phases, without forming microemulsions.

Figure 1:
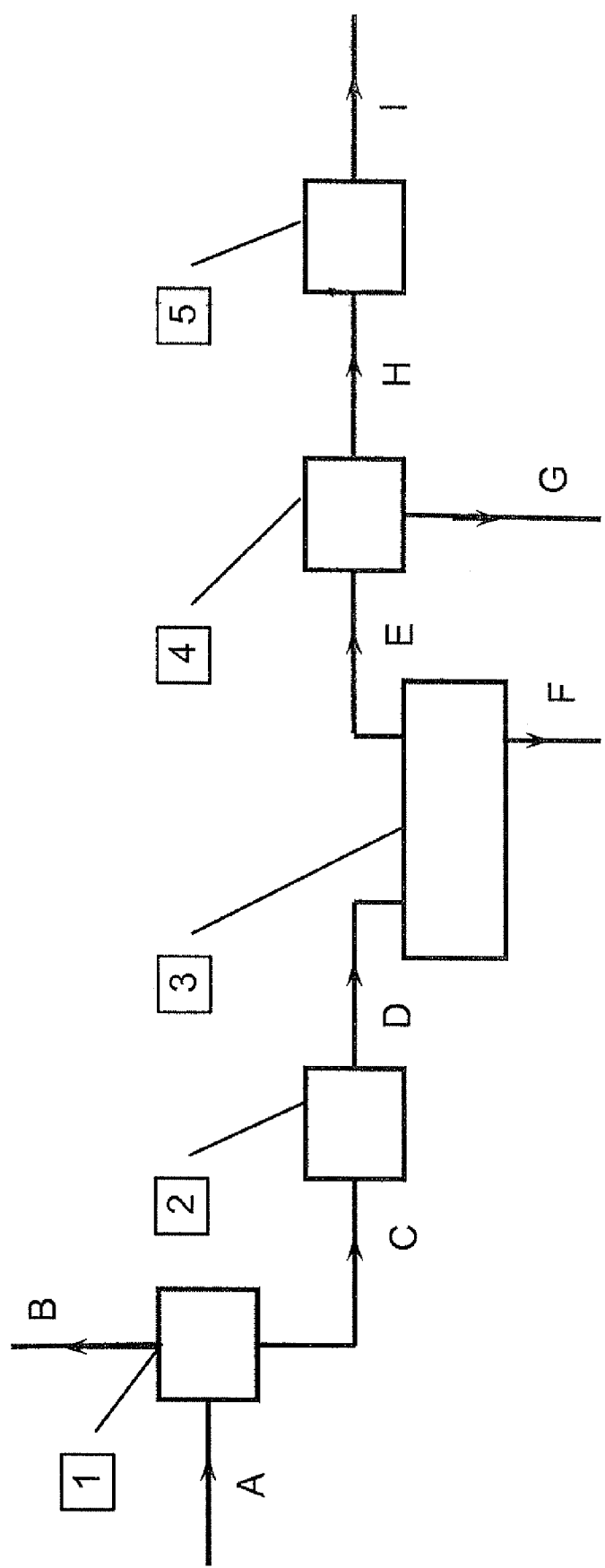
FIG. 1 diagrammatically shows part of the Esterfip-H™ process as described in the prior art, and FIG. 2 diagrammatically shows part of the Esterfip-H™ process comprising the improvement provided according to the present invention.
Figure 2:
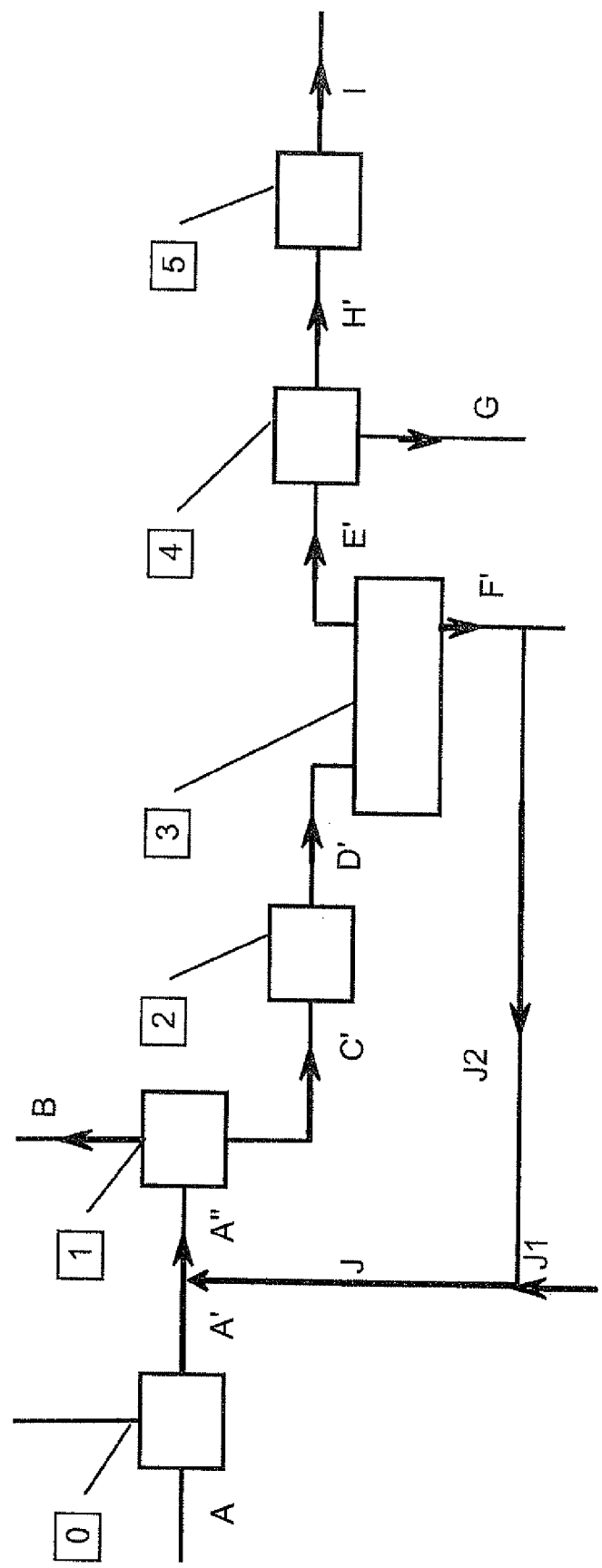

FIG. 2 shows a diagram of a particular embodiment of the improved method according to the present invention.

The facility wherein this embodiment is implemented comprises:

a reaction section (not shown in the figure) at the outlet of which an effluent comprising alkyl esters, glycerol, partly converted triglycerides and alcohol is obtained, possibly a zone (O) intended for pre-evaporation of part of the alcohol contained in stream A, at the outlet of which a stream A' is obtained, a line through which a glycerin phase (stream J) of purity above 50% by mass is injected into alcohol-depleted stream A', an evaporation zone (1) allowing to separate the alcohol (stream B) and the effluent comprising alkyl esters, glycerol and partly converted triglycerides (stream C'), a heat exchanger (2) allowing stream C' to be cooled, at the outlet of which a stream D' is obtained, a decanter (3) allowing to separate the supernatent ester phase (stream E') and the glycerin phase (stream F'), and possibly a residual glycerin separation zone (4, 5).

Advantageously, this separation zone can be a coalescer (4) for separating the residual insoluble glycerin and/or a solid adsorption zone (5) for separating the soluble glycerol from the ester phase.

Stream A comes from the reaction section and it predominantly consists of alkyl esters, alcohol, glycerol and partly converted triglycerides.

The stage carried out in zone (O) is an optional stage of pre-evaporation of part of the excess alcohol. This stage can be carried out without generating an insoluble glycerin phase and it allows to obtain a stream A' containing alkyl esters, glycerol, partly converted triglycerides and a lesser amount of alcohol.

A glycerin-enriched stream J is then mixed with stream A'. This mixture makes up stream A" that is sent to alcohol evaporation zone (1). A stream B corresponding to the evaporated alcohol and a stream C' comprising alkyl esters, glycerol and partly converted triglycerides are obtained at the outlet of this zone.

This stream J represents 0.1 to 100% by volume of the flow rate of stream A from the reaction zone, or of stream A' if a pre-evaporation stage was carried out. Preferably, it represents 1 to 50% by volume of the flow rate of stream A.

Stream J contains at least 50% by mass of glycerol and preferably 75% by mass, more preferably 90% by mass, The glycerin used for this addition stage consists of streams J1 and/or J2.

Stream J1 corresponds to a glycerin phase from an exterior source, whose purity is above at least 50% by mass, preferably above 70% by mass and more preferably above 90% by mass.

Stream J2 corresponds to part of stream and it consists of glycerin whose purity is at least 50% by mass, preferably above 75% by mass and more preferably above 90% by mass, directly withdrawn from decanter (3).

More preferably, stream J comes entirely from the recycle (stream J2) of the glycerin withdrawn from decanter (3) and it represents part of stream F'.

Stream C' is then subjected to cooling in a heat exchanger (2) in order to reduce the proportion of glycerol dissolved in the ester phase.

During the stage of alcohol evaporation and of cooling of the stream comprising alkyl esters, glycerol and partly converted triglycerides, the glycerin made insoluble adds to the proportion of glycerin phase already present, corresponding to the amount injected through stream J. Thus, stream D' leaving heat exchanger (2) contains a larger amount of glycerin in form of bigger drops that are thereafter readily decanted in the ester phase and glycerin phase separation stage.

Stream D' is then sent to decanter drum (3) where the main part of the separation of the two phases (ester and glycerin) takes place.

One advantage of the present invention is that it allows the size of the decanter to be decreased thanks to the droplet size increase.

A glycerin stream F' is extracted from the decanter bottom while the ester phase is collected at the top of the drum (stream E').

According to the method of the present invention, stream E', as a result of the improved decantation, contains less glycerin carried along in the ester phase.

Advantageously, after the decantation stage, stream E' can be sent to a coalescer (4). Considering that glycerin decantation is improved, this equipment will be of more reduced size. A glycerin stream G' is withdrawn at the bottom point of the coalescer.

Ester stream H' containing practically no and preferably no more insoluble glycerin extracted from coalescer (4) can be advantageously sent to zone (5) for a solid adsorption stage. During this stage, the alternation of adsorption/regeneration cycles undergone by the solids is thus less frequent and their life is therefore increased. The solid regeneration stages are carried out with a lesser amount of solvent. The economy of the processing chain is thus greatly improved.

If decantation allows to separate all of the insoluble glycerin, the ester stream from decanter (3) can then for example be advantageously sent directly to a solid adsorption zone (5) without requiring an additional coalescence stage.

Several measuring and/or calculating methods are necessary for characterizing the glycerin population in the ester phase from the drop size point of view.

When the ester phase only contains dissolved glycerol, it is completely limpid. When it contains insoluble glycerin droplets, it tends to become cloudy. It is thus possible to visually observe the limit between the cloudy phase and the limpid phase: this limit is defined as the decantation front. Monitoring of the decantation front and notably of the rate of displacement of this front allows to estimate the size of the drops present in the ester phase. A sample of an emulsion consisting of the continuous ester phase containing glycerin droplets is therefore placed in a graduated cylinder. Monitoring the displacement time of the decantation front allows to calculate a rate of displacement for this front. Standard values correlating the size of the drops and the rate of displacement of the decantation front allow to deduce the droplet sizes among the smallest ones.

Decantation times of the order of several hours imply very small drop sizes of the order of some microns.

Drop size measurements are also confirmed by optical microscopy, by arranging samples of the emulsion under a variable-power optical microscope. The various sizes of the glycerin droplets that coexist in the ester-glycerin mixture are thus directly measured. The sizes thus measured also allow to check the results obtained by monitoring the decantation front.

Complementary numerical fluid mechanics calculations allow to follow the trajectories of the droplets in the decanter drum. It is thus possible to estimate the separation efficiency of the decanter for the glycerin droplets flowing in with the ester stream. The size of the droplets being furthermore a parameter of the calculation, it can be varied until a separation corresponding to the separation really observed in the decanter is obtained.

The invention claimed is:

1. A method of producing fatty acid alkyl esters and glycerin implementing, in a reaction section, a set of transesterification reactions between a vegetable or animal oil and an aliphatic monoalcohol, and using a heterogeneous solid catalyst, comprising:
    a) adding a stream of a glycerin phase of purity above 50% by mass in effluent from the reaction section comprising alkyl esters, glycerol, partly converted triglycerides and alcohol,
    b) evaporation of excess alcohol of said effluent,
    c) cooling, and;
    d) decanting the glycerin phase and obtaining a supernatent ester phase.

2. A method as claimed in claim 1, wherein glycerin phase addition is preceded by pre-evaporation of part of the excess alcohol.

3. A method as claimed in claim 1, wherein the added glycerin phase has a flow rate of 0.1 to 100% by volume of the flow rate of the stream.

4. A method as claimed in claim 3, wherein said flow rate represents 1 to 50% by volume of the flow rate of the stream.

5. A method as claimed in claim 1, wherein the added glycerin phase partly comes from recycle of glycerin withdrawn from the decanter.

6. A method as claimed in claim 1, wherein the added glycerin phase entirely comes from recycle of glycerin withdrawn from the decanter.

7. A method as claimed in claim 1, wherein the added glycerin has a purity above 75% by mass.

8. A method as claimed in claim 1, wherein said supernatent ester phase (stream E') is sent to a coalescer (4) from which a glycerin phase (stream G) is withdrawn at the bottom point thereof and an ester phase (stream H') is withdrawn.

9. A method as claimed in claim 8, wherein the ester phase (stream H') is sent to a zone (5) for at least one solid adsorption stage.

10. A facility wherein the method of producing fatty acid alkyl esters and glycerin as claimed in claim 1 is implemented, comprising:
    a reaction section at the outlet of which an effluent stream A comprising alkyl esters, glycerol, partly converted triglycerides and alcohol is obtained,
    optionally a zone (O) pre-evaporating of part of the alcohol contained in stream A, at the outlet of which a stream A' is obtained,
    a line through which a glycerin phase (stream J) of purity above 50% by mass is injected into alcohol-depleted stream A' forming stream A",
    an evaporation zone (1) receiving stream A' separating the alcohol (stream B) and an effluent comprising alkyl esters, glycerol and partly converted triglycerides (stream C') of stream A",
    a heat exchanger (2) cooling stream C', at the outlet of which a stream D' is obtained,
    a decanter (3) receiving stream D' and separating stream D' into a supernatent ester phase (stream E') and a glycerin phase (stream F'), and
    optionally stream E' enters a residual glycerin separation zone (4, 5).

11. A facility as claimed in claim 10, wherein the separation zone is present and comprises a coalescer (4) and/or a solid adsorption zone (5).

12. A method as claimed in claim 1, wherein the added glycerin has a purity above 90% by mass.

* * * * *